United States Patent
Adam et al.

(10) Patent No.: US 11,826,742 B1
(45) Date of Patent: Nov. 28, 2023

(54) EFFECTIVE HETEROGENEOUS CATALYST OF ZNO—TIO2 COATED BY COPPER (II) BIS-SCHIFF BASE HYDRAZONE COMPLEX FOR THE ORGANIC OXIDATION PROCESSES

(71) Applicant: KING FAISAL UNIVERSITY, Al-Ahsa (SA)

(72) Inventors: Mohamed Shaker S. Adam, Al-Ahsa (SA); Amel Taha, Al-Ahsa (SA); Mohamed M. Makhlouf, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/220,416

(22) Filed: Jul. 11, 2023

(51) Int. Cl.
| | |
|---|---|
| *C07C 45/29* | (2006.01) |
| *B01J 31/22* | (2006.01) |
| *B01J 21/06* | (2006.01) |
| *B01J 37/02* | (2006.01) |
| *B01J 37/04* | (2006.01) |
| *B01J 23/06* | (2006.01) |
| *B01J 35/00* | (2006.01) |
| *B01J 35/08* | (2006.01) |
| *B01J 37/03* | (2006.01) |

(52) U.S. Cl.
CPC ......... *B01J 31/2217* (2013.01); *B01J 21/063* (2013.01); *B01J 23/06* (2013.01); *B01J 35/0013* (2013.01); *B01J 35/08* (2013.01); *B01J 37/0219* (2013.01); *B01J 37/0221* (2013.01); *B01J 37/0236* (2013.01); *B01J 37/038* (2013.01); *B01J 37/04* (2013.01); *C07C 45/294* (2013.01); *B01J 2231/763* (2013.01); *B01J 2531/16* (2013.01)

(58) Field of Classification Search
CPC ... C07C 45/294; B01J 31/2217; B01J 21/063; B01J 23/06; B01J 37/0215; B01J 37/04
See application file for complete search history.

(56) References Cited

FOREIGN PATENT DOCUMENTS

CN 108003008 A 5/2018

OTHER PUBLICATIONS

Saremi, S. G. et al., "Schiff Base Mn (III) and Co (II) Complexes Coated on Co Nanoparticles: An Efficient and Recyclable Magnetic Nanocatalyst for H2O2 Oxidation of Sulfides to Sulfoxides", Journal "The Royal Society of Chemistry", 2018, 8, 3889-3898.
Charles, A. et al., "Synthesis of Copper(II) Schiff Base Complex and Its Mixed Thin Layer With ZnO Nanoparticles", Journal, "Iranian Journal of Chemistry and Chemical Engineering", vol. 40, No. 3 (2021), pp. 758-764.
Amina, M. et al., "Biogenic Green Synthesis of MgO Nanoparticles Using Saussurea Costus Biomasses for a Comprehensive Detection of Their Antimicrobial, Cytotoxicity Against MCF-7 Breast Cancer Cells and Photocatalysis Potentials", Journal "PLOS ONE", 15(8), 2020.
Yusuf, T. L. et al., "Design of New Schiff-Base Copper(II) Complexes: Synthesis, Crystal Structures, DFT Study, and Binding Potency Toward Cytochrome P450 3A4", Journal "ACS Omega", 2021, 6, 21, 13704-13718.

*Primary Examiner* — Sikarl A Witherspoon
(74) *Attorney, Agent, or Firm* — Nath, Goldberg & Meyer; Richard C. Litman (57) ABSTRACT

A new heterogeneous catalyst for various organic oxidation processes and a method of making the same by a successful immobilization of a copper (II) bis-Schiff base hydrazone complex on the surface of a composite $ZnO$—$TiO_2$ to afford as active catalyst $CuL_2Cl_2@ZnO$—$TiO_2$. This novel catalyst can be used to selectively oxidize benzyl alcohol to benzaldehyde.

14 Claims, 8 Drawing Sheets

EFFECTIVE HETEROGENEOUS CATALYST OF ZNO—TIO2 COATED BY COPPER (II) BIS-SCHIFF BASE HYDRAZONE COMPLEX FOR THE ORGANIC OXIDATION PROCESSES

BACKGROUND

1. Field

The disclosure of the present patent application relates to preparation methods for effective and selective heterogeneous ZnO—TiO$_2$ catalysts coated by a copper (II) bis-Schiff base hydrazone complex salt as an effective heterogeneous catalyst for the oxidation of organic compounds.

2. Description of the Related Art

Homogeneous metal-Schiff base complex catalysts have been represented as highly effective catalysts in many organic transformations, e.g., oxidation of thiols, sulfides, alcohols, and olefins. However, compared to heterogeneous analogues, they lack promotion of temperature stability, reusability, recoverability and strong separability in various catalytic processes. Presently, many reported homogeneous metal-Schiff base complex catalysts have been converted into heterogeneous ones by immobilizing covering processes on nanostructural materials of metal oxides, mixed metal oxides, or alloys, e.g., ZnO, NiO, CuO, Fe$_2$O$_3$, Fe$_3$O$_4$, TiO$_2$, SiO$_2$, Al$_2$O$_3$, Fe$_3$O$_4$@TiO$_2$, Fe$_3$O$_4$@SiO$_2$, or Cu in modern catalytic applicability. Accordingly, such processes of obtaining heterogeneous catalysts have successfully been achieved to modify the catalytic features of certain applied homogenous catalysts to result in improved recovery, separation, dispersibility, recyclization, and thermal stability of the nanostructured species of metal-Schiff base complex catalysts in certain catalytic systems.

On the other hand, the most distinguished disadvantages of the heterogeneous catalysts with covered immobilized metal Schiff base complex catalysts are the high loaded amount and less catalytic action compared to the homogeneous analogues, as well as their high cost of preparation. The most important significant property for the heterogeneous catalysts is the specific surface area, for that most of metal oxides have been combined with iron oxides to modify their specific surface area, especially for high magnetic nanoparticles, e.g., Fe$_3$O$_4$ nanoparticles as TiO$_2$@Fe$_3$O$_4$ and SiO$_2$@Fe$_3$O$_4$.

Thus, new low-cost copper (II) bis-Schiff base hydrazone complex salts capable as effective and selective heterogeneous catalysts solving the aforementioned problems are desired.

SUMMARY

The present subject matter relates to new, low-cost copper (II) bis-Schiff base hydrazone complex salts as effective and selective heterogeneous catalysts for the oxidation of benzyl alcohol using an aqueous H$_2$O$_2$ in water. Specifically, the present subject matter relates to a new useful catalyst, CuL$_2$Cl$_2$@ZnO—TiO$_2$, in this regard.

Accordingly, an object of the present subject matter is to provide a construction of a new heterogeneous catalyst for various organic oxidation processes by a successful immobilization of a copper (II) bis-Schiff base hydrazone complex on the surface of a ZnO—TiO$_2$ composite to obtain as active catalyst CuL$_2$Cl@ZnO—TiO$_2$.

In an embodiment, the present subject matter relates to a method of coating a copper (II) bis-Schiff base hydrazone complex on zinc oxide and titanium oxide (ZnO—TiO$_2$) nanostructured particles, the method comprising: mixing a solution of a CuL$_2$Cl$_2$ complex having the formula:

with a suspended solution of ZnO—TiO$_2$ nanoparticles; obtaining suspended ZnO—TiO$_2$ nanoparticles coated with the CuL$_2$Cl$_2$ complex; and drying the suspended ZnO—TiO$_2$ nanoparticles coated with the CuL$_2$Cl$_2$ complex to obtain the copper (II) bis-Schiff base hydrazone complex on zinc oxide and titanium oxide (ZnO—TiO$_2$) nanostructured particles as a CuL$_2$Cl$_2$@ZnO—TiO$_2$ nanocomposite.

In a further embodiment, the present subject matter relates to a copper (II) bis-Schiff base hydrazone complex (CuL$_2$Cl$_2$) on zinc oxide and titanium oxide (ZnO—TiO$_2$) nanostructured particles comprising a CuL$_2$Cl$_2$@ZnO—TiO$_2$ nanocomposite, prepared according to the present methods.

In another embodiment, the present subject matter relates to a CuL$_2$C12@ZnO—TiO$_2$ nanocomposite comprising a copper (II) bis-Schiff base hydrazone complex (CuL$_2$Cl$_2$) on zinc oxide and titanium oxide (ZnO—TiO$_2$) nanostructured particles, the CuL$_2$Cl$_2$ complex having the formula:

In still another embodiment, the present subject matter relates to a method for oxidizing benzyl alcohol, the method comprising: adding the $CuL_2Cl_2@ZnO\text{—}TiO_2$ nanocomposite of claim 9 and benzyl alcohol to acetonitrile to obtain a mixture; adding an aqueous solution of $H_2O_2$ to the mixture at a temperature of about 70° C. to about 90° C.; and oxidizing the benzyl alcohol to obtain benzaldehyde.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

In an embodiment, the present subject matter relates to a method of coating a copper (II) bis-Schiff base hydrazone complex on zinc oxide and titanium oxide ($ZnO\text{—}TiO_2$) nanostructured particles, the method comprising: mixing a solution of a $CuL_2Cl_2$ complex having the formula:

with a suspended solution of ZnO—TiO$_2$ nanoparticles; obtaining suspended ZnO—TiO$_2$ nanoparticles coated with the CuL$_2$Cl$_2$ complex; and drying the suspended ZnO—TiO$_2$ nanoparticles coated with the CuL$_2$Cl$_2$ complex to obtain the copper (II) bis-Schiff base hydrazone complex on zinc oxide and titanium oxide (ZnO—TiO$_2$) nanostructured particles as a CuL$_2$Cl$_2$@ZnO—TiO$_2$ nanocomposite. During the process, the color of the suspended ZnO—TiO$_2$ can gradually change from paly gray to dark gray. Prior to drying, the nanoparticles can be washed one or several times with acetonitrile.

This coating process can be further seen by referring to the following scheme. The technical scheme involves the deprotonation of the para-carboxylic group with bonding to the ZnO—TiO$_2$ nanoparticle forming a new composite heterogeneous catalyst "CuL$_2$Cl$_2$@ZnO—TiO$_2$".

In certain embodiments, the solution of the CuL$_2$Cl$_2$ complex can comprise CuL$_2$Cl$_2$ mixed in acetonitrile. In other embodiments, the suspended solution of ZnO—TiO$_2$ nanoparticles can comprise the ZnO—TiO$_2$ nanoparticles in acetonitrile.

In a further embodiment, the step of obtaining suspended ZnO—TiO$_2$ nanoparticles coated with the CuL$_2$Cl$_2$ complex can comprise refluxing the solution of the CuL$_2$Cl$_2$ complex mixed with the suspended solution of ZnO—TiO$_2$ nanoparticles at about 70° C. to about 90° C. for at least about 24 hours. In this regard, this step can be conducted at a temperature of about 70° C., about 75° C., about 80° C., about 85° C., about 90° C., or about 80° C.

In certain embodiments, the CuL$_2$Cl$_2$ complex in the solution of the CuL$_2$Cl$_2$ complex can be obtained by a method comprising: pouring a methanolic solution of copper chloride dihydrate into a mixture of methanol and a Schiff base hydrazone ligand (HL) having the formula:

to obtain a mixed solution; heating the mixed solution for at least about 3 hours at a temperature of about 50° C. to about 70° C. to obtain a heated mixed solution; and cooling the heated mixed solution and removing the methanol to obtain the CuL$_2$Cl$_2$ complex. In this regard, this step can be conducted at a temperature of about 50° C., about 55° C., about 60° C., about 65° C., about 70° C., or about 60° C. In this regard, the copper chloride solution can be added to the HL mixture dropwise at room temperature. This mixed solution can then be stirred while it is heated, at which point the color can change from yellow to brown. Once the methanol is removed, the product can be purified as an orange residue that can be recrystallized in methanol to obtain a pure CuL$_2$Cl$_2$ at a yield of about 75%.

The reaction scheme for this step of the process can be seen as follows:

In another embodiment in this regard, the Schiff base hydrazone ligand (HL) can be obtained by a method comprising: reacting equimolar amounts of isatin hydrazide and 4-formylbenzoic acid in methanol for at least about 2 hours at a temperature of about 70° C. to about 90° C.; and removing the methanol to obtain the Schiff base hydrazone ligand (HL). In this regard, this step can be conducted at a temperature of about 70° C., about 75° C., about 80° C., about 85° C., about 90° C., or about 80° C. Further, a few drops of glacial acetic acid can be added to the reaction mixture. The reaction, in an embodiment, can occur under refluxing, and can result in a yellow end product, demonstrating complete formation of the ligand. The obtained product, after the methanol is removed, can be recrystallized in ethanol and dried in an oven to obtain a yield of about 90%.

The reaction scheme for this step of the process can be seen as follows:

In a further embodiment, the ZnO—TiO$_2$ nanoparticles in the suspended solution of the ZnO—TiO$_2$ nanoparticles can be obtained by a method comprising: mixing *Saussurea costus* with Zn(NO)$_2$·6H$_2$O (80 mL of 0.2 mmol) to form ZnO nanoparticles; adding the ZnO nanoparticles to a suspended solution of TiO$_2$ in ethanol to obtain a suspended precipitate; and filtering, washing, and drying the suspending precipitate to obtain ZnO—TiO$_2$ nanoparticles. The *Saussurea costus* used herein can be the roots of the plant.

The initial solution to form the ZnO nanoparticles can be at a pH of about 10, with the pH of this solution being controlled using an aqueous solution of about 1.0 mol dm$^{-3}$ KOH. This solution can be stirred at about 1000 rpm and at about 70° C. to about 80° C. for at least about 2 hours. Likewise, the suspended solution of TiO$_2$ can be prepared by ultrasonicating titanium dioxide in ethanol for about 15 minutes. The ZnO nanoparticles can then be added dropwise to the TiO$_2$ suspended solution with continuous stirring for at least about 24 hours and at about 70° C. to about 80° C. The obtained precipitate can be calcined in an oven for about 2 hours, for example, in an about 250° C. oven.

In a further embodiment, the present subject matter relates to a copper (II) bis-Schiff base hydrazone complex (CuL$_2$Cl$_2$) on zinc oxide and titanium oxide (ZnO—TiO$_2$) nanostructured particles comprising a CuL$_2$Cl$_2$@ZnO—TiO$_2$ nanocomposite, prepared according to the present methods.

In another embodiment, the present subject matter relates to a CuL$_2$Cl$_2$@ZnO—TiO$_2$ nanocomposite comprising a copper (II) bis-Schiff base hydrazone complex (CuL$_2$Cl$_2$) on zinc oxide and titanium oxide (ZnO—TiO$_2$) nanostructured particles, the CuL$_2$Cl$_2$ complex having the formula:

In this regard, the nanocomposite can comprise a mixture of spherical and irregular nanoparticles.

In still another embodiment, the present subject matter relates to a method for oxidizing benzyl alcohol, the method comprising: adding the CuL$_2$Cl$_2$@ZnO—TiO$_2$ nanocomposite of claim 9 and benzyl alcohol to acetonitrile to obtain a mixture; adding an aqueous solution of H$_2$O$_2$ to the mixture at a temperature of about 70° C. to about 90° C.; and oxidizing the benzyl alcohol to obtain benzaldehyde. In this regard, this process can be conducted at a temperature of about 70° C., about 75° C., about 80° C., about 85° C., about 90° C., or about 80° C.

In further embodiments in this regard, the method can be conducted under aerobic conditions. Further, the method can obtain the benzaldehyde at a yield of about 91%. The remaining 9% can be divided into 8% of benzoic acid and 1% unknown side products. In other embodiments, the method can have a 99% conversion with a 92% selectivity. In certain embodiments, the benzyl alcohol and the H$_2$O$_2$ can be used in an about 1:3 molar ratio.

The present teachings are illustrated by the following examples.

EXAMPLES

In these examples, most of the reagents were from Sigma-Aldrich, Fluka, and Acros. All compounds were characterized using Elemental analyses and NMR resonance, FT-IR, electronic, as well as EI-mass spectroscopies.

Structural and surface conformation of the studied nanomaterials was accomplished by FT-IR spectra, XRD (X-ray powder diffraction) SEM (field emission scan electron microscope), EDS (the energy-dispersive X-ray spectroscopy), HR-TEM (high resolution transmission electron microscope), and TGA (thermogravimetric analyses).

Example 1

Preparation of Schiff Base Hydrazone Ligand (HL)

Schiff base ligand (HL) was formed form the reaction of isatin hydrazide (0.32 g, 2.0 mmol) with 4-formylbenzoic acid (0.30 g, 2.0 mmol) in equimolar amounts in 25 mL methanol with reflux for approximately 2 h at 80° C. in the presence of a few drops of glacial acetic acid. At the end of refluxing, a yellow color was observed in the reaction media with TLC check for achieving the complete formation of the ligand. After that, methanol was evacuated to give a crude product of HL that recrystallized in ethanol and dried in an oven to afford yield percentage 90%, as 0.53 g.

In methanol, 4-formylbenzoic acid condensed with isatin hydrazide provided the Schiff base hydrazone ligand (HL).

Example 2

Synthesis of Copper (II) Bis-Schiff Base Hydrazone Complex

A methanolic solution (25 mL) of copper chloride dihydrate (2.0 mmol, 0.34 g) was dropwise poured into 45 mL methanol having HL (4.0 mmol, 0.58 g) therein at room temperature. Then, the mixed solution was heated with magnetic stirring for 3 h at 60° C. with color changing from yellow to brown. With TLC, the complexation was monitored. At the end and with cooling to the room temperature, methanol was removed by vacuum and the obtained residue was collected. From purification, the orange residue was recrystallized in methanol to award a pure $CuCl_2L_2$, yielding 1.08 g, or 75%.

Figure 1:
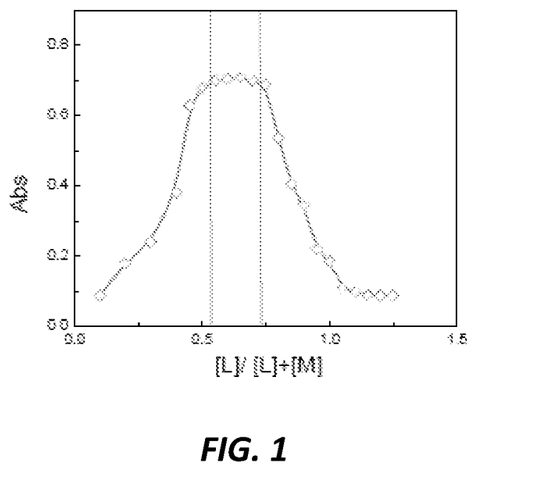
FIG. 1 is continuous variation plot for the stoichiometric molar ratios for $CuL_2Cl_2$ formed from a HL reaction with $Cu^{2+}$ ions with [L] and $[M]=1\times10^{-5}$ mol $dm^{-3}$ at 25° C.

HL was coordinated to $Cu^{2+}$ ions in a water/methanol mixture in 2:1 equivalent amounts, respectively, giving $CuL_2Cl_2$. HL and $CuL_2Cl_2$ had observable yields with 90 and 75% of 0.53 and 1.08 g, respectively. The equivalent ratios of $Cu^{2+}$ ions to HL were probed using the spectrophotometric continuous variation in methanol, as shown in FIG. 1. The results show that each $CuL_2Cl_2$ molecule was formed in a 1:2 ratio with the ion of $Cu^{2+}$ ion to two molecules of HL. Table 1 presents the elemental analyses of the novel complex ($CuL_2Cl_2$).

Example 3

Fabrication of ZnO—TiO$_2$

*Saussurea costus* roots were used to fabricate ZnO nanoparticles coated by $TiO_2$. Mixing 20 mL of *Saussurea costus* with $Zn(NO_3)_2 \cdot 6H_2O$ (80 mL of 0.2 mmol) formed ZnO nanoparticles. At pH≈10, the mixed solution was controlled using an aqueous solution of 1.0 mol dm$^{-3}$ KOH, then magnetic stirring with a rate of 1000 rpm at 70-80° C. for 2 h was adjusted.

After that, to prepare a suspended solution of nanoparticles of $TiO_2$, in 100 mL ethanol, titanium dioxide 5.0 g was ultrasonicated for 15 min with Elmasonic S150 device of a model of TEVOTECH. It was followed by dropwise pouring of the ZnO nanoparticles solution into the later suspended solution of $TiO_2$ with continuous stirring for 24 h at 70-80° C. At the end of stirring, the final suspended precipitate was extracted by filtration and then washed several times with $H_2O$ and then dried to get $ZnO/TiO_2$ powder. The obtained precipitate was calcined at 250° C. in an oven for 2 h.

Example 4

Immobilization of $CuL_2Cl_2$ Complex on $ZnO/TiO_2$ $CuL_2Cl_2$ complex was immobilized on ZnO—$TiO_2$ nanoparticles by mixing a solution of 0.2 g $CuL_2Cl_2$ in 50 ml acetonitrile with a suspended solution of 0.2 g ZnO—$TiO_2$ in 50 ml acetonitrile. The resulting solution was kept under reflux (at 80° C. for 24 h) in an ultrasonic bath (TEVOTECH S150) at about 20 kHz. The color of the suspended ZnO—$TiO_2$ gradually changed from pale gray to dark gray. The suspension of ZnO—$TiO_2$ coated by $CuL_2Cl_2$ was accumulated by filtration and then washed several times with acetonitrile. Finally, the $CuL_2Cl_2$@ZnO—$TiO_2$ nanocomposite was dried.

Example 5

Characterization of Obtained Compounds

Figure 2:
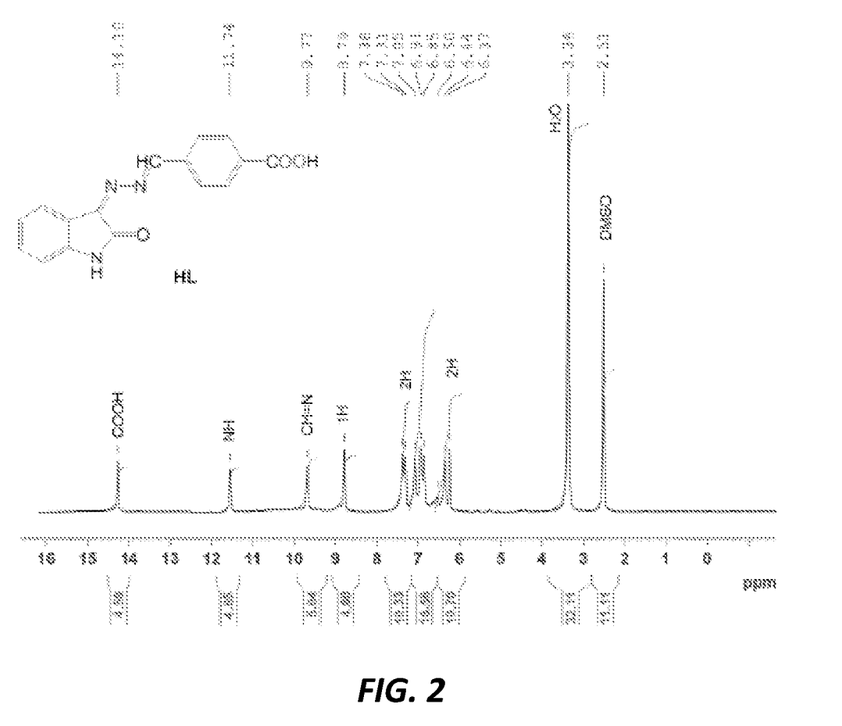
FIG. 2 is a 1H NMR spectra of HL in DMSO-d6 at 25° C.
Figure 3:
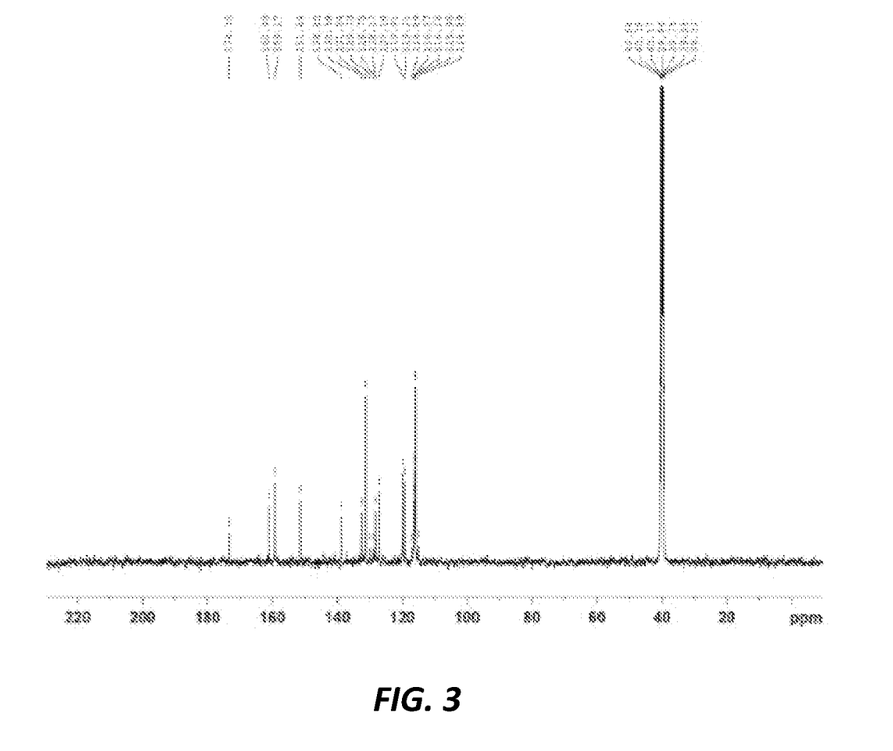
FIG. 3 is a 13C NMR spectra of HL in DMSO-d6 at 25° C.

The $^1$HNMR spectrum of HL is presented in FIG. 2, and the $^{13}$CNMR spectrum of HL is presented in FIG. 3.

Figure 4A:
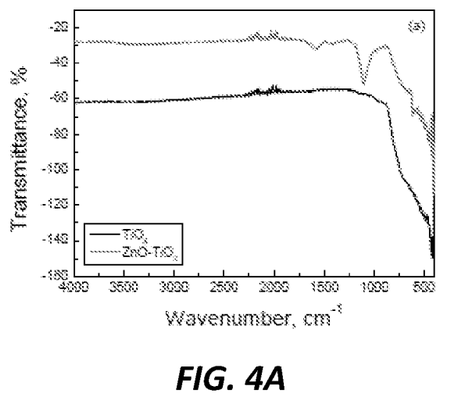
FIGS. 4A-B show IR spectra of (A) $TiO_2$ and its composited $ZnO@TiO_2$ nanoparticles; and (B) $CuL_2Cl_2$ and its composite $CuL_2Cl_2@ZnO\text{—}TiO_2$ at room temperature.
Figure 4B:
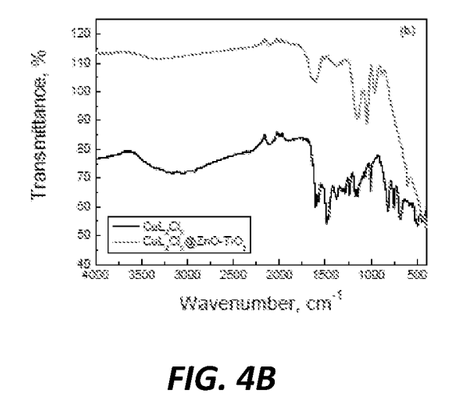

FIG. 4 displays the FT-IR spectra of (A) $TiO_2$ and its composited ZnO@$TiO_2$ nanoparticles, (b) $CuL_2Cl_2$ and its composite $CuL_2Cl_2$@ZnO—$TiO_2$ at room temperature.

TABLE 1

CHN percentage analyses and UV Vis. Spectrum of $1.0 \times 10^{-5}$ mol · dm$^{-3}$ solutions in methanol at 25° C. of $CuL_2Cl_2$

| Comp. (M.W.) | CHN Analyses, % | | | Electronic spectra | | |
|---|---|---|---|---|---|---|
| | C | H | N | $\lambda_{max}$, nm | Assign. | $\varepsilon$, mol$^{-1}$ · cm$^{-1}$ |
| $CuL_2Cl_2$ (721.01 g · mol$^{-1}$) | 53.53 (53.31) | 3.36 (3.08) | 11.32 (11.66) | 281 | Π→π*n→π* | 11466 |
| | | | | 362 | L→MCT | 8695 |
| | | | | 553 | d-d | 2299 |

Figure 5:
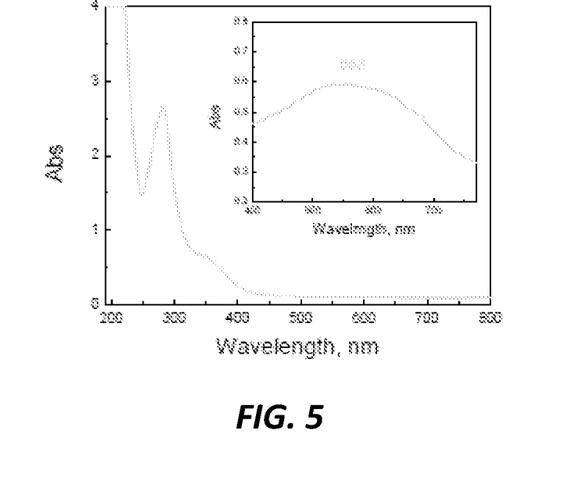
FIG. 5 shows the UV-Vis. spectra of methanolic solutions of $CuL_2Cl_2$ at 25° C.
Figure 6:
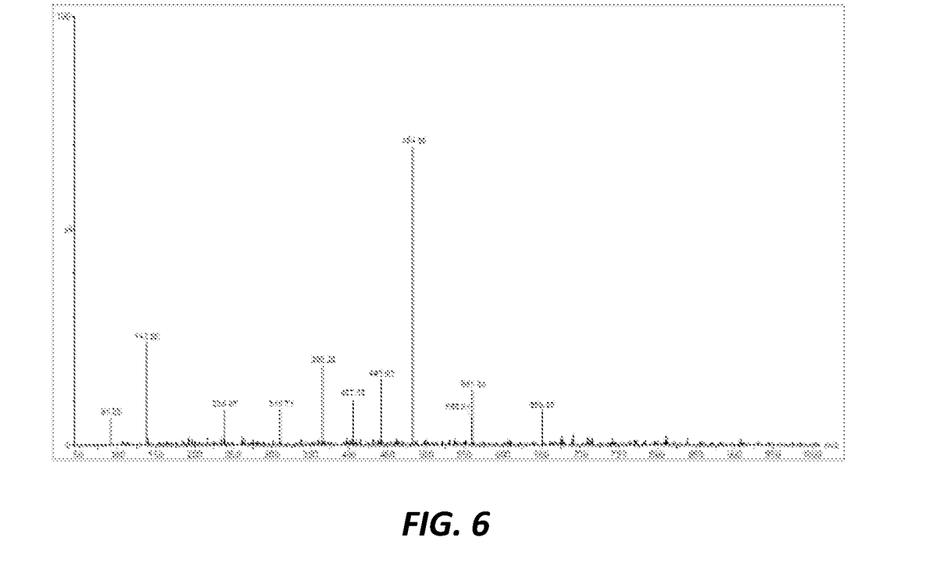
FIG. 6 shows EI-MS spectra of $CuL_2Cl_2$ in methanol at 25° C.

The characteristic electronic transition spectra in methanolic solutions of $CuL_2Cl_2$ were given in FIG. 5. Similarly, the EI-Mass spectroscopy of $CuL_2Cl_2$ was studied in methanol and given in FIG. 6.

Figure 7A:
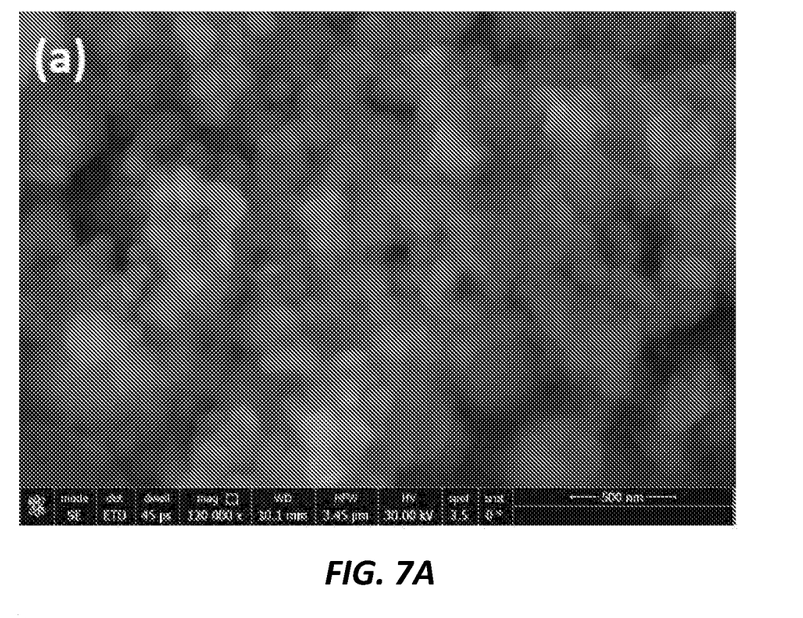
FIGS. 7A-B show FESEM images of (A) $TiO_2\text{—}ZnO$; and (B) $CuL_2Cl_2@ZnO\text{—}TiO_2$ nanoparticles.
Figure 7B:
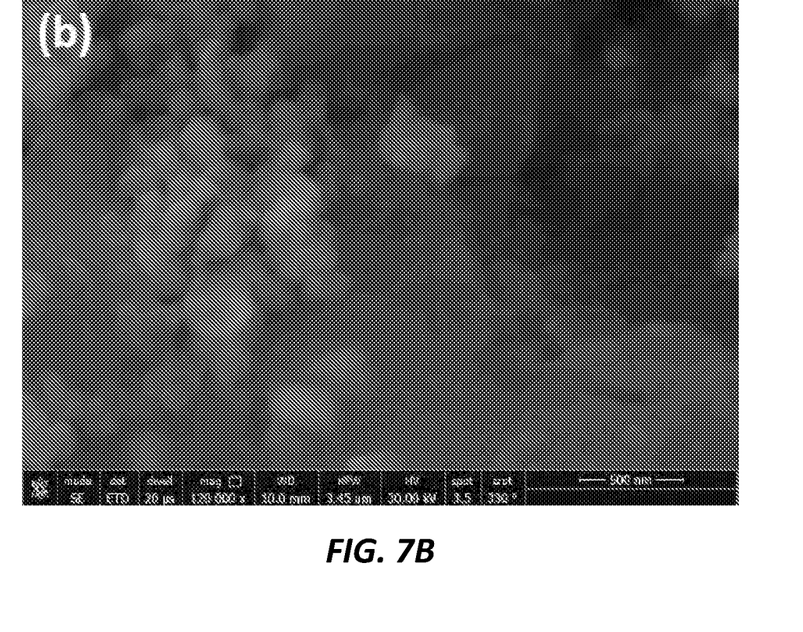
Figure 8A:
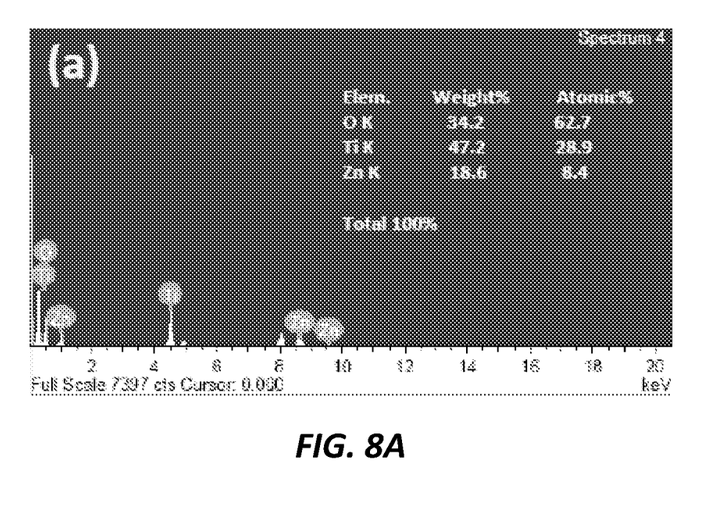
FIGS. 8A-B show EDX spectra of (A) $TiO_2\text{—}ZnO$; and (B) $ZnO\text{—}TiO_2@ CuL_2Cl_2$ nanoparticles.
Figure 8B:
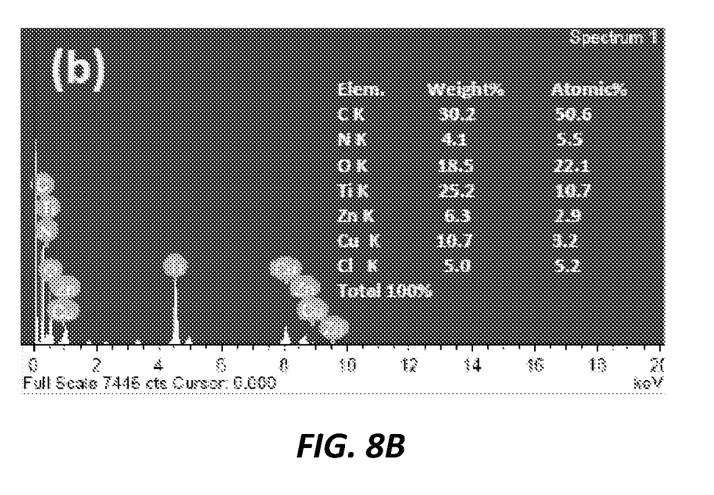

FIGS. 7A-B shows FESEM images of $ZnO$—$TiO_2$ and $CuL_2Cl_2@ZnO$—$TiO_2$ nanocomposites with different magnifications by using a FESEM microscope. The EDS spectra of $ZnO$—$TiO_2$ and $CuL_2Cl_2@ZnO$—$TiO_2$ nanocomposites reveal a normal distribution of the constituent elements of Zn, Ti, Cu, O, N, Cl, and C, as shown in FIGS. 8A-B.

Figure 9A:
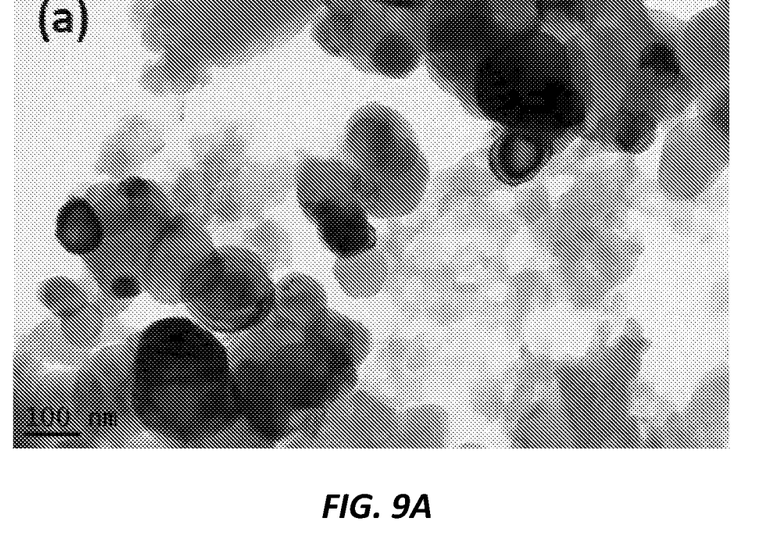
FIGS. 9A-B show HRTEM micrographs of (A) $TiO_2\text{—}ZnO$; and (B) $ZnO\text{—}TiO_{2@} CuL_2Cl_2$ nanoparticles.
Figure 9B:
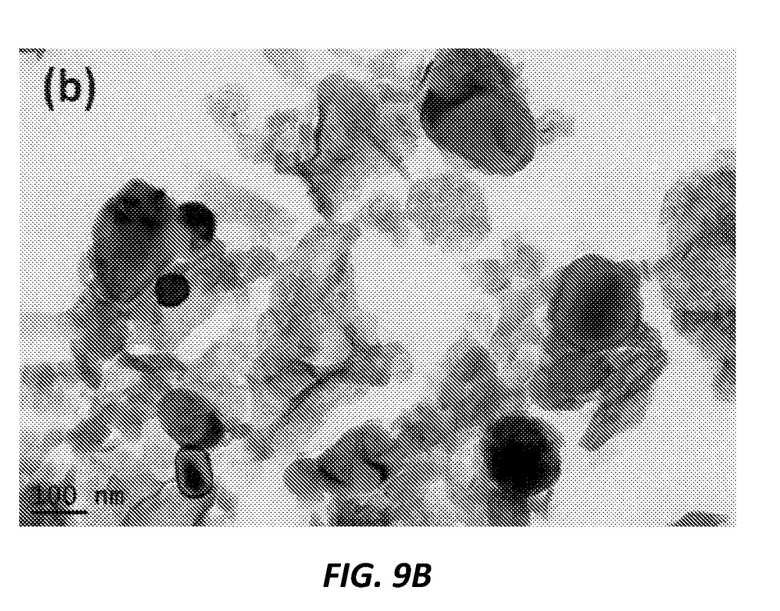
Figures 10A, 10B, 10C, 10D:
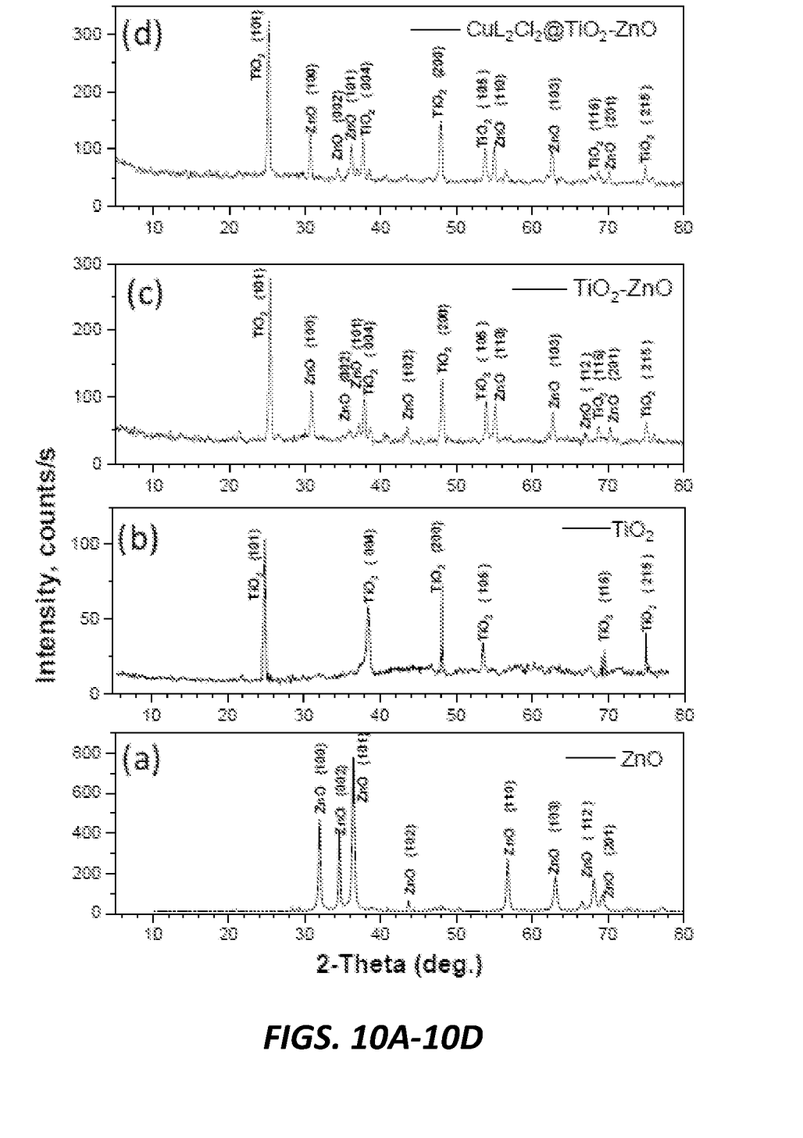
FIGS. 10A-D show XRD patterns of (A) ZnO, (B) $TiO_2$, (C) $TiO_2\text{—}ZnO$, and (D) $ZnO\text{—}TiO_2@CuL_2Cl_2$ nanoparticles.

FIGS. 9A-B depicts HRTEM images of $ZnO@TiO_2$ and $ZnO$—$TiO_2@$ $CuL_2Cl_2$ nanocomposites. The images displayed the internal formation structure composed of different sizes of spherical and irregular nanoparticles.

The X-ray diffraction (XRD) patterns of $ZnO@TiO_2$, and $ZnO$—$TiO_2@CuL_2Cl_2$ nanocomposites are shown in FIGS. 10A-D.

Example 5

Catalytic Oxidation of Alcohols

Under an aerobic atmosphere, in 10 mL acetonitrile was added 20 mg of $CuL_2Cl_2@ZnO$—$TiO_2$ (heterogeneous catalyst) and 1.0 mmol benzyl alcohol. After that, 3.0 mmol of $H_2O_2$ (an aqueous solution of 30%) was poured leisurely at the applied temperature (80° C.). In the catalytic system with solvent-free conditions, $H_2O$ or chloroform, the catalytic effectiveness of the studied catalysts was investigated.

The heterogeneous catalyst $ZnO$—$TiO_2@CuL_2Cl_2$ was involved with the redox protocols of benzyl alcohol using an aqueous $H_2O_2$ in acetonitrile. Their effectiveness was deduced by the illustrated percentages of conversion and productivity yield of the oxide product of the selective one, benzaldehyde and the unselective ones, benzoic acid, at 80° C. A GC-MS device was applied to deduce the yielding amount of the oxide product and recorded in Table 2. Furthermore, TON values were calculated and tabulated in Table 2.

We claim:

1. A method of coating a copper (II) bis-Schiff base hydrazone complex on zinc oxide and titanium oxide ($ZnO$—$TiO_2$) nanostructured particles, the method comprising:
   mixing a solution of a $CuL_2Cl_2$ complex having the formula:

with a suspended solution of $ZnO$—$TiO_2$ nanoparticles;
   obtaining suspended $ZnO$—$TiO_2$ nanoparticles coated with the $CuL_2Cl_2$ complex; and
   drying the suspended $ZnO$—$TiO_2$ nanoparticles coated with the $CuL_2Cl_2$ complex to obtain the copper (II) bis-Schiff base hydrazone complex on zinc oxide and titanium oxide ($ZnO$—$TiO_2$) nanostructured particles as a $CuL_2Cl_2@ZnO$—$TiO_2$ nanocomposite.

2. The method of claim 1, wherein the solution of the $CuL_2Cl_2$ complex comprises $CuL_2Cl_2$ mixed in acetonitrile.

TABLE 2

Solvent effect on the catalytic oxidation of benzyl by $H_2O_2$ catalyzed by of $ZnO$—$TiO_2@CuL_2Cl_2$.

| Solvent[a] | Catalyst | Amount (%)[b] | | | | Conversion (%) | Selectivity (%) | TON |
|---|---|---|---|---|---|---|---|---|
| | | BA | BZ | BO | Side products | | | |
| Acetonitrile (AN) | $ZnO$—$TiO2@$ | 3 | 91 | 4 | 1 | 97 | 94 | 18.2 |
| Solvent-free | $CuL_2Cl_2$ | 0 | 94 | 7 | 3 | 100 | 94 | 18.8 |
| Chloroform | | 7 | 83 | 7 | 3 | 93 | 89 | 17.8 |
| $H_2O$ | | 15 | 66 | 15 | 4 | 85 | 78 | 13.2 |

[a]1.0 mmol (benzyl alcohol, BA) in 10 mL solvent + 0.05 g $VOL_2@TiO_2$—$ZnO$ + 3.00 mmol $H_2O_2$ at the optimum of time and temperature.
[b]Percentage of selective product (benzaldehyde, BZ) + benzoic acid (BO) is detected by GC/MS.

The yield percentage of benzaldeyde was evaluated as 91% with 92% selectivity of 99% conversion. The 9% was divided into 8% of benzoic acid and 1% unknown side products.

It is to be understood that the nanocomposite is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

3. The method of claim 1, wherein the suspended solution of $ZnO$—$TiO_2$ nanoparticles comprises the $ZnO$—$TiO_2$ nanoparticles in acetonitrile.

4. The method of claim 1, wherein the step of obtaining suspended $ZnO$—$TiO_2$ nanoparticles coated with the $CuL_2Cl_2$ complex comprises refluxing the solution of the $CuL_2Cl_2$ complex mixed with the suspended solution of $ZnO$—$TiO_2$ nanoparticles at about 70° C. to about 90° C. for at least about 24 hours.

5. The method of claim 1, wherein the $CuL_2Cl_2$ complex in the solution of the $CuL_2Cl_2$ complex is obtained by a method comprising:

pouring a methanolic solution of copper chloride dihydrate into a mixture of methanol and a Schiff base hydrazone ligand (HL) having the formula:

to obtain a mixed solution;
heating the mixed solution for at least about 3 hours at a temperature of about 50° C. to about 70° C. to obtain a heated mixed solution; and
cooling the heated mixed solution and removing the methanol to obtain the $CuL_2Cl_2$ complex.

6. The method of claim 5, wherein the Schiff base hydrazone ligand (HL) is obtained by a method comprising:
reacting equimolar amounts of isatin hydrazide and 4-formylbenzoic acid in methanol for at least about 2 hours at a temperature of about 70° C. to about 90° C.; and
removing the methanol to obtain the Schiff base hydrazone ligand (HL).

7. The method of claim 1, wherein the $ZnO$—$TiO_2$ nanoparticles in the suspended solution of the $ZnO$—$TiO_2$ nanoparticles are obtained by a method comprising:
mixing *Saussurea costus* with $Zn(NO)_2 \cdot 6H_2O$ (80 mL of 0.2 mmol) to form ZnO nanoparticles;
adding the ZnO nanoparticles to a suspended solution of $TiO_2$ in ethanol to obtain a suspended precipitate; and
filtering, washing, and drying the suspending precipitate to obtain $ZnO$—$TiO_2$ nanoparticles.

8. Copper (II) bis-Schiff base hydrazone complex ($CuL_2Cl_2$) on zinc oxide and titanium oxide ($ZnO$—$TiO_2$) nanostructured particles comprising a $CuL_2Cl_2@ZnO$—$TiO_2$ nanocomposite, prepared according to the method of claim 1.

9. A $CuL_2Cl_2@ZnO$—$TiO_2$ nanocomposite comprising a copper (II) bis-Schiff base hydrazone complex ($CuL_2Cl_2$) on zinc oxide and titanium oxide ($ZnO$—$TiO_2$) nanostructured particles, the $CuL_2Cl_2$ complex having the formula:

10. The nanocomposite of claim 9, comprising a mixture of spherical and irregular nanoparticles.

11. A method for oxidizing benzyl alcohol, the method comprising:
adding the $CuL_2Cl_2@ZnO$—$TiO_2$ nanocomposite of claim 9 and benzyl alcohol to acetonitrile to obtain a mixture;
adding an aqueous solution of $H_2O_2$ to the mixture at a temperature of about 70° C. to about 90° C.; and
oxidizing the benzyl alcohol to obtain benzaldehyde.

12. The method of claim 11, wherein the method is conducted under aerobic conditions.

13. The method of claim 11, wherein the method obtains the benzaldehyde at a yield of about 91%.

14. The method of claim 11, wherein the method has a 99% conversion with a 92% selectivity.

* * * * *